United States Patent [19]
Ervin

[11] Patent Number: 4,743,556
[45] Date of Patent: May 10, 1988

[54] PETRI DISH

[75] Inventor: Klon R. Ervin, Glen Arm, Md.

[73] Assignee: Curtin Matheson Scientific, Inc., Houston, Tex.

[21] Appl. No.: 50,112

[22] Filed: May 15, 1987

[51] Int. Cl.$^4$ .............................................. C12M 1/22
[52] U.S. Cl. ...................................... 435/297; 435/296
[58] Field of Search ............... 435/296, 297, 298, 299, 435/300, 287

[56] References Cited

U.S. PATENT DOCUMENTS

| | | | |
|---|---|---|---|
| 2,144,255 | 1/1939 | Carpenter | 435/297 |
| 2,361,992 | 11/1944 | Cantor | 435/297 |
| 3,198,713 | 8/1965 | McCormick . | |
| 3,248,302 | 4/1966 | Machin | 435/298 |
| 3,630,849 | 12/1972 | Land | 435/287 |
| 3,649,463 | 3/1972 | Buterbaugh . | |
| 3,684,660 | 8/1972 | Kereluk et al. | 435/297 |
| 4,160,700 | 7/1979 | Boomus et al. . | |
| 4,321,330 | 3/1982 | Baker et al. . | |
| 4,569,647 | 2/1986 | McCormick | 435/287 |

Primary Examiner—Samuel Scott
Assistant Examiner—H. A. Odar
Attorney, Agent, or Firm—Silverman, Cass, Singer & Winburn, Ltd.

[57] ABSTRACT

A petri dish includes a bottom container member having a circumferential groove located in the bottom corner thereof. The groove facilitates the distribution of liquid culture media during the filling operation, assists in retaining the periphery of the solidified media in place to increase shelf-life, and provides a pleasing visual perception as to the media thickness when the petri dish is viewed from the side. The cover member includes an upstanding rib located on a top surface thereof, such that upon stacking the petri dish with another of like construction, the exterior surface of the circumferential groove and the upstanding rib cooperate to facilitate stacking. Also, the respective top and bottom walls of the cover and bottom container being 30% thinner than their associated side wall portions to provide in a savings in fabrication material.

18 Claims, 3 Drawing Sheets

FIG. I

PETRI DISH

BACKGROUND OF THE INVENTION

The present invention relates to an improved microorganism culturing dish, commonly referred to as a petri dish. More particularly, the present invention is directed towards an improved petri dish, with several newly provided and improved characteristics. The petri dish of the present invention is, relative to the prior art, less expensive to produce, uses less materials, is easily stackable, and provides both unexpected results with respect to the even distribution of the culturing media during manufacture and increased shelf-life.

Prior art petri dishes generally include a bottom container and a mating cover member. The bottom container usually takes the form of a shallow truncated cylinder, while the cover member likewise takes the form of complementary truncated cylinder having a somewhat enlarged inside diameter to allow the cover member to fit over the bottom container.

Although the structure of a petri dish is quite simple, it must perform its intended function as efficiently and inexpensively as possible. Ideally, the petri dish should be a shallow rigid container which is easily manipulable by a technician with respect to manual placement and removal of the cover member. Also, the petri dish should efficiently receive and distribute liquid nutrient media during the manufacturing process so that a uniform layer of solidified media with a continuous meniscus with the side wall of the bottom container is obtained. In this regard, the interior configuration of the bottom container should not impede the distribution of the liquid nutrient media during filling. For example, it is known to provide machinery that physically wobbles the bottom container during filling to assist in the even distribution of the liquid media prior to hardening to form the media layer on the bottom of the container. Further, the dish must be susceptible to stacking, the stacked dishes interrelating with one another sufficiently to permit convenient transport in the stacked configuration.

Examples of prior petri dishes are contained in the following U.S. Pat. Nos.: 4,160,700 to Boomus et al; 3,198,713 to McCormick; and 3,649,463 to Buterbaugh. The Boomus dish has a radial flange on its lid to facilitate single-handed manipulation for removal of the lid, and a mating arrangement between a lid and the bottom surface of a petri dish stacked thereon. The McCormick petri dish, on the other hand, is a lid-less system. McCormick proposes the stacking of several bottom members such that each successive dish provides a lid for the preceding dish in the stack. Buterbaugh is similar to Boomus in that the Buterbaugh dish and its features are directed towards ease of manual manipulation of the disk. As such, Buterbaugh discloses a dish bottom portion having an outwardly extended peripheral flange with a series of inwardly extending slots. The flange is configured so as to facilitate manual grasping the dish.

SUMMARY OF THE INVENTION

In view of the above, it is an object of the present invention, among others, to provide a petri dish which is easily manipulated by one hand, leaving the other hand free to add a specimen or sample to the bottom portion of the petri dish.

It is another object of the present invention to provide a petri dish which uses less materials in its fabrication than previously proposed petri dishes.

It is another object of the present invention to provide a petri dish which is easily stackable and therefore transportable in comparatively large numbers.

It is a further object of the present invention to provide a petri dish which evenly spreads and retains a liquid culture media, such as Agar, on the inner bottom surface of the bottom member as part of the dish filling process.

It is a still further object of the present invention to provide a petri dish which increases the shelf life of the completed petri dish by increasing the contact surface area of the nutrient media with the bottom portion of the container.

In view of these objects, and others, the present invention provides a petri dish that has side wall portions of its bottom and top members which are of a conventional thickness but where the bottom and top wall portions are approximately 30% thinner to diminish the amount of starting material used to fabricate the complete petri dish. Further, a petri dish according to the present invention provides a rib/groove interengagement between a lid top surface and bottom container member bottom surface to facilitate stacking and transport of the stacked dishes. A circumferential trough or groove is provided around the inner corner of a bottom member to function as a distribution channel which assists and the even spreading of the fluidic culture media and the formation of a uniform meniscus during manufacture. The circumferential groove also assists in locking the solidified media in place and prevents 'lifting' of the media as a consequence of evaporation of its moisture content. Additionally, the circumferential groove provides a visual indication of thickness for the media in the petri dish.

Other objects and further scope of applicability of the present invention will become apparent from the detailed description to follow, taken in conjunction with the accompanying drawings, in which like parts are designated by like reference characters.

DESCRIPTION OF THE PREFERRED EMBODIMENT

Figure 1:
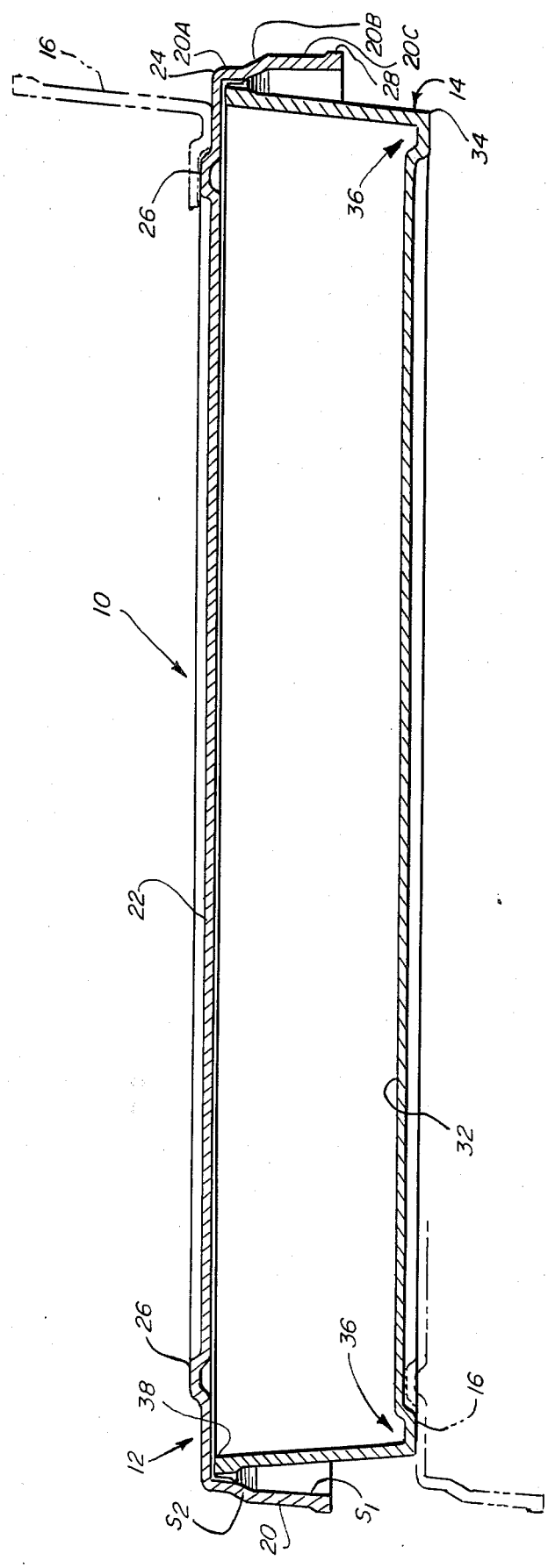
FIG. 1 is a cross sectional view of a petri dish in accordance with the present invention taken along a diameter section line.

As shown in FIG. 1, a petri dish in accordance with the present invention is shown in cross section and designated generally therein by the reference character 10. As shown, the petri dish 10 includes a cover 12 mounted upon a bottom member 14. The cover 12 and the bottom member 14 are fabricated using a conventional unitary molding process using an organic, preferably transparent, polymer such as polystyrene or polyparamethyl styrene.

The cover 12 includes a circular top 22 and an integrally formed peripheral side wall 20. The circular top 22 has, as an integral part thereof, an upstanding annular rib 26 adjacent the side wall 20. The annular rib 26, as shown in FIG. 1, assists in engaging the bottom member 14 of the next higher petri dish 10 in a stack of petri dishes. A transition corner 24 connects the circular top 22 to the side wall 20. The side wall 20 is defined by three sub-wall sections including a sub-wall 20A at the corner 24 and which is substantially perpendicular to the circular top 22, an outwardly flared sub-wall 20B, and another somewhat longer outwardly flared sub-wall 20C. A thickened rim portion 28 is provided along the entire periphery of the remote end of the sub-wall 20C to provide a measure of structural rigidity. As explained more fully below in relationship to FIG. 7, the outwardly flared sub-walls 20B and 20C define conically inclined inner surfaces $S_1$ and $S_2$ that provide a conically converging 'lead-in' for the smaller diameter sub-wall 20A to facilitate re-liding of the cover 12 during the manufacturing process, after filling of the bottom member 14 with culture media, and during normal use. The use of the outwardly flared sub-walls 20B and 20C thus reduces the need to precisely position the cover 12 during re-liding, and the cylindrical sub-wall 20A limits the lateral clearance between the cover 12 and the bottom member 14 to enhance stackability.

The bottom member 14 includes a circular bottom wall 32 and an outwardly flared, upstanding side wall 30. The side wall 30 has a thickened rim portion 38 at its upper end to add a measure of rigidity to the bottom member 14. Similarly, a corner 34 connects the side wall 30 to the bottom wall 32. The bottom member 14 is shaped to include an annular, downwardly extending rib 16 adjacent the corner 34 at the lower end of the side wall 30 so that the major portion of the bottom wall 32 is indented relative to the rib 16. The rib 16 defines an annular distribution and retention groove 36 on the interior side of the bottom wall 32. The external rib 16 of the bottom wall 32 interengages the rib 26 formed in the top wall 12 of the cover 12, as mentioned above. This interengaging rib configuration facilitates stacking of the petri dishes 10 and subsequent transport of the stacked dishes from one location to another. The aligning function provided by the rib interface is best illustrated in dotted line illustration in FIG. 1.

Figure 2:
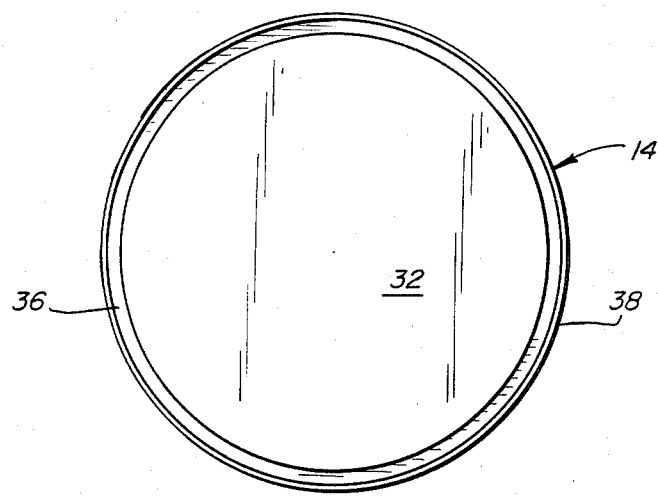
FIG. 2 is a plan view of a bottom container member according to the present invention.
Figure 3:
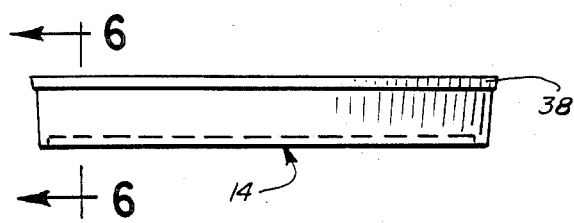
FIG. 3 is an elevational view of a bottom member according to the present invention.

The bottom member 14 is shown in plan and elevational views in FIGS. 2 and 3, respectively. The bottom member 14 has a maximum diameter "$D_b$" of between 3 and 4 inches and, in a preferred embodiment 3.46 inches. Also, the depth "$d_b$" of the bottom member 14 is generally one-half an inch and in a preferred embodiment 0.52 inches.

Figure 4:
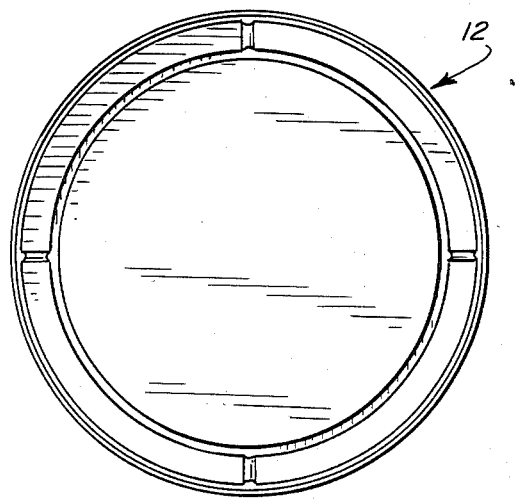
FIG. 4 is a plan view of a cover member according to the present invention.
Figure 5:
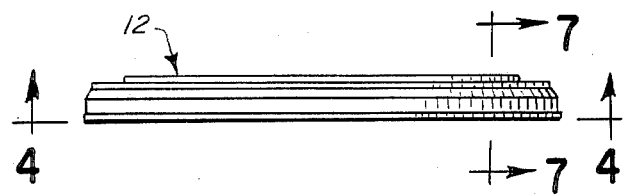
FIG. 5 is an elevational view of a cover member according to the present invention.

FIGS. 4 and 5 show views of the cover 12 corresponding to the views of the bottom member 14 of FIGS. 2 and 3. The cover 12 is sized to be approximately two-tenths of an inch greater in diameter than the bottom member 14. In this preferred embodiment, the diameter reference "$D_c$" is 3.66 inches. The cover 12 is not as deep as the bottom member 14 and has a depth "$d_c$" somewhat less than ½ an inch. In a preferred embodiment, the depth reference "$d_c$" is 0.32 inches.

Figure 6:
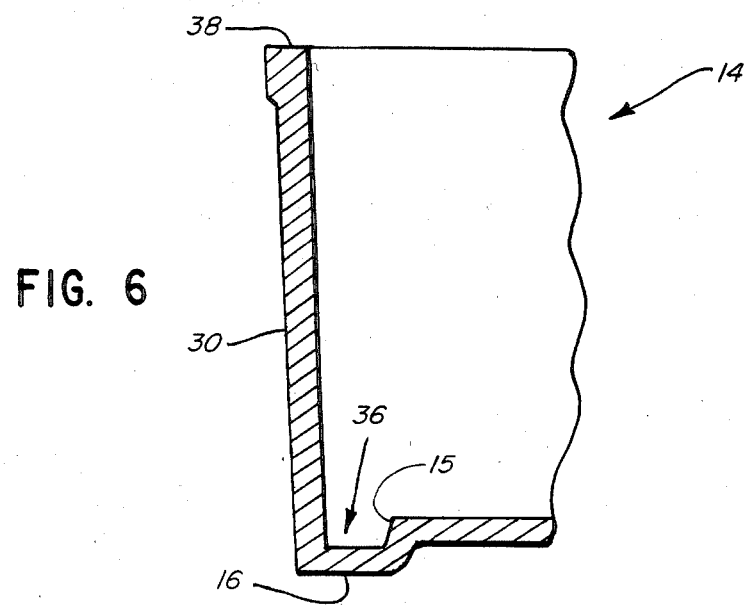
FIG. 6 is an enlarged view of detail 6—6 as shown in FIG. 3.

FIG. 6 illustrates detail 6—6 of FIG. 3, which corresponds to the circumferential rim 38, the side wall 30, and the groove 36 of the bottom member 14. The bottom member 14 generally comprises a thickened rim portion 38 blending into the side wall 30 connecting to the corner 34 to the groove 36 with a small transition step 15 up to the circular bottom wall 32. In the preferred embodiment the side wall 30 is flared outwardly at about an angle of 12° from the vertical and the remainder of the bottom member would be constructed as follows: The depth of the thickened rim portion 340 would be 0.049 inches; while the entire depth of the thickened rim portion 342 (including the transition taper) would be 0.08 inches; the wall thickness of the side wall 30 would be 0.03 inches; the entire depth of the bottom member 344 would be 0.52 inches; the groove bottom wall-thickness 346 would be 0.025 inches; the slope of the surface of the groove side wall at the step 15 would be 15 degrees from the vertical; the slope of the outside surface of the groove side wall would be 12 degrees; the radius 352 between the groove outside wall surface and the bottom wall outside surface would be 0.02 inches; and the thickness of the bottom wall 32 would be 0.023 inches. The respective diametric references 360–366 would be dimensioned as follows: 360 would be 3.46 inches; 362 would be 3.38 inches; 364 would be 3.16 inches; 366 would be 3.16 inches.

The unique advantages disclosed in the aforementioned preferred embodiment, are as follows: the side wall portion 30 is 25 percent thicker than bottom wall portion 32. Such a relationship lends to a perceived feeling of strength and rigidity when the petri dish bottom is grasped. Further, the bottom member 14 generally looks more substantial when the side walls 30 are thicker than the bottom wall 32. Also, by dimensioning the bottom wall 32 to be thinner than the side wall 30, a proportionate savings in the fabrication materials results.

The side wall 30 also has a thickened rim member 38. This thickened rim portion provides enhanced rigidity to the side wall 30 without the necessity of thickening the entire side wall.

The groove 36 provides several unique and unexpected advantages. Firstly, the groove 36 gives a visual perception of increased depth of the petri dish 10 and of the nutrient media contained with in the dish. Secondly, the groove 36 provides enhanced rigidity to the bottom member 14 as a whole so that the bottom member 14 has a perceived rigidity. Thirdly, the groove 36, as an external annular rib 16, interacts with the rib 26 of the cover 12 and aids in the stacking of the petri dishes. Fourthly, the groove 36 achieves the unexpected result of assisting in the even spreading the bacterial culturing medium in the bottom of the petri dish 10 and the formation of a uniform meniscus. During manufacture of the petri dish 10, between 15 and 18 milliliters of heated and liquefied culture media, i.e., Agar, is introduced into the bottom member 14 of a petri dish at a temperature of approximately 110° F. Since the culture media rapidly cools and congeals to form a solidified media, the liquid media must be spread in a time efficient manner. In one system, a specially designed machine wobbles or tips the petri dish 10 in various directions to achieve spreading and the formation of a uniform meniscus with the side wall. This spreading step, of course, adds to the cost of manufacture. In the context of the present invention, the circumferential groove 36 serves as a channel to draw and distribute the rapidly cooling culture media around the peripheral edges of the petri dish 10 bottom member to reliably form a uniform meniscus and thus fully distribute the liquid media prior to its solidification. As such, the culture media is thus evenly spread over the bottom member bottom surface prior to cooling. The need for a tipping function during the spreading step is reduced or minimized. Further, when the culture media cools, a tendency exists for 'lifting' to occur due to increased surface tension along the peripheral edges. The annular groove 36 provides an additional thickness of culture media at these curl or lift susceptible edges. As a result, edge curling is much less likely. Because the media has a high moisture content, the media dries with time with the radially inward shrinking stresses increasing with increasing radius. The groove 36, by assisting in retaining the solidified media, effectively extends the useful life of the culture media due to its ability to stay flat on the bottom of the petri dish 10.

Figure 7:
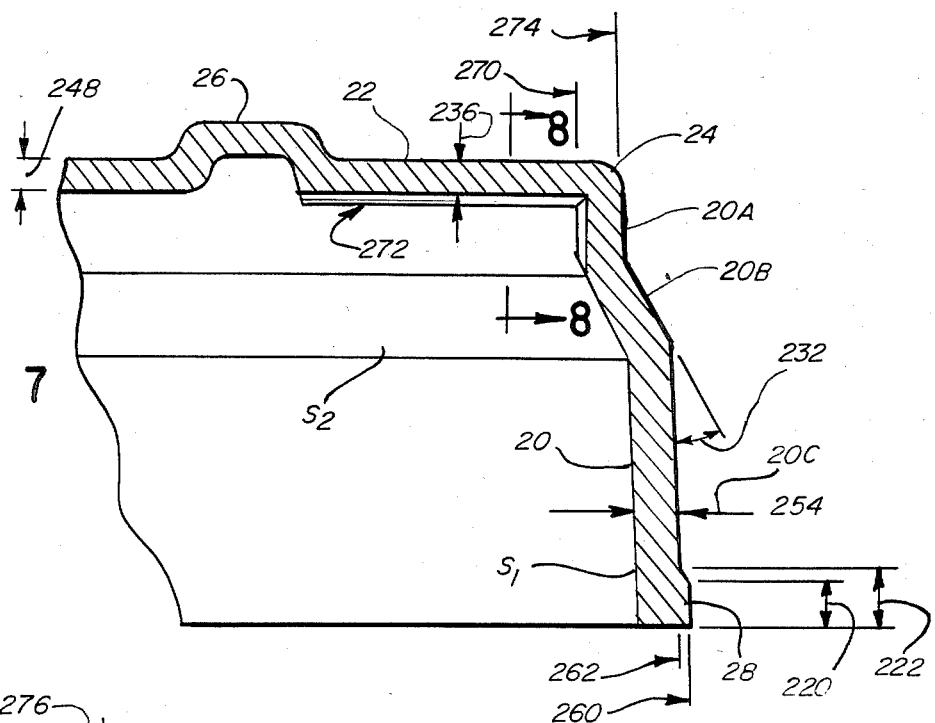
FIG. 7 is an enlarged view of detail 7—7 of FIG. 5.

FIG. 7 illustrates an enlarged peripheral edge portion of the cover 12 shown in FIG. 5. The cover 12 has the following major components: a thickened rim 28 connected to the side wall portion 20 having a depending step therein leading to a corner 24 which in turn is attached to the circular top 22. As mentioned above, the side wall 20 includes sub-wall 20A, 20B, and 20C. The sub-wall 20A is substantially perpendicular to the circular top 22, the outwardly flared sub-wall 20B is flared outward at about an angle of 60° from the vertical and the somewhat longer sub-wall 20C is flared outwardly at about an angle of 12°. The sub-wall 20C provides an interior lead-in surface $S_2$ while the sub-wall 20B provides another interior lead-in surface $S_1$. The lead-in surfaces make the re-liding of the bottom member 14 very convenience since initial positioning of the two components need not be a precise as with other petri dishes. Once an initial, slightly mis-aligned engagement is accomplished, the cover 12 is slide into proper engagement because of the presence of the lead-in surfaces $S_1$ and $S_2$.

The circular top 22 incorporates the annular rib 26 discussed above. The cover 12 also includes standoff members 272. The standoff members 272 provide free air passage between the interior of the petri dish 10 and the surrounding ambient atmosphere by maintaining a gap between the circular top 22 and the upper rim 38 of the lower member 14.

In the preferred embodiment, the cover 12 has the following dimensional characteristics: the depth 220 of the rim 38 would be 0.03 inches; the depth 222 of the rim portion including the transition taper would be 0.04 inches; the wall thickness 254 would be 0.03 inches; the angle 232 of the step portion would be 60 degrees; the top wall thickness 236 would be 0.025 inches; the wall thickness 248 of the rib 26 and the remaining top wall portions would be 0.023 inches; the internal depth of rib 26 would be 0.03 inches.

The following diametric relationships are also preferred: the overall diameter of the cover member 260 would be 3.66 inches; 262 would be 3.635 inches; 270 would be 3.485 inches; and 274 would be 3.544 inches.

The following advantages are noted in the preferred configuration of the cover 12: firstly, the construction results in a savings of starting materials; secondly, the described construction results in a rigid cover member; thirdly, the ribbed top surface results in superior stacking ability; and, fourthly, the presence of the lead-in surface enhances the ease with which the petri dish can be re-lidded.

Although the material savings could be considered as modest for a single petri dish 10, the overall material savings of 25–30 percent resulting from the thinner top and the bottom wall construction of the present petri dish results in a substantial saving in large manufacturing quantities. The present 25–30 percent savings can, over a conventional run of 10 million petri dishes, result in a saving of starting material equal to 3 million petri dishes. Further, the reduced-material dish of the present invention retains all of the desirable characteristics of a full thickness petri dish, and creates several more desirable characteristics. In particular, the internal groove 36 gives the appearance of increased depth of the culture media when viewed from the side of the petri dish 10 and also significantly aids in culture media distribution and retention. The internal groove 36, as an external rib 16, also aids in the stacking of the petri dishes 10 and subsequent transport in a stacked configuration.

Figure 8:
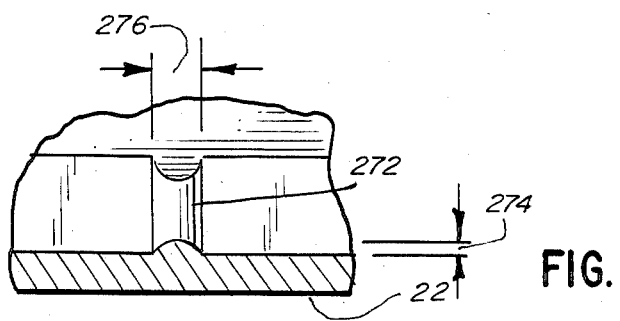
FIG. 8 is a cross sectional view inverted of the cover member along section 8—8 of FIG. 7.

FIG. 8 illustrates the enlarged cross-sectional view along line 8—8 of FIG. 7. More particularly, standoff 272 is shown as a small linear radiused protrusion from circular top 22. Since section 8—8 looks toward the depending inner surface of side wall 20, the standoff 272 is truncated at a 59° angle along a continuation of the angle 252. As such, the standoff 272 has an edge portion which extends below the inner rim of the depending side wall portion. In a preferred embodiment, there would exist a plurality of standoff members with four being a minimum. Also, in a preferred embodiment, the standoff 272 would be radiused at 0.018 inches, with a protruding depth 274 of 0.006 inches, and a width 276 of 0.030 inches. The standoff 272 merely prevents any sealing from taking place between the top and the bottom members of the petri dish 10. As such, air may flow in and out of the petri dish 10 container as required.

While the preferred embodiment of the petri dish 10 is disclosed as having an annular groove at the base of the side wall, as can be appreciated, the groove can also be located interiorly adjacent to the side wall. Additionally, with first and second flared sub-walls have been describes as part of the cover, additional sub-walls can be provided.

Thus it will be appreciated from the above that as a result of the present invention, a highly effective petri dish is provided by which the principal objective, among others, is completely fulfilled. It will be equally apparent and is contemplated that modification and/or changes may be made in the illustrated embodiment without departure from the invention. Accordingly, it is expressly intended that the foregoing description and accompanying drawings are illustrative of preferred embodiments only, not limiting, and that the true spirit and scope of the present invention will be determined by reference to the appended claims and their legal equivalent.

What is claimed is:

1. A petri dish for receiving a solidifiable liquid media, comprising:
a first component having a bottom wall having top and bottom surfaces and an upstanding circumferentially extending side wall at the periphery of the bottom wall, said bottom wall having a circumferentially extending trough formed in the top surface adjacent the intersection of the side wall and the periphery of the bottom wall, said trough comprising means for receiving and distributing solidifiable liquid media during filling of the dish to assist in even spreading of the solidifiable liquid media across the bottom wall of the dish to ensure formation of a uniform media meniscus at the juncture of the side and bottom walls and for retaining the solidified media in place.

2. The petri dish of claim 1, further comprising a second component having a top wall and a depending side wall at the periphery of the top wall and so dimensioned to overlie and cover said first component.

3. The petri dish of claim 2, wherein said depending side wall of said second component is flared outwardly to define at least one interior lead-in surface for guiding said second component onto said first component.

4. The petri dish of claim 3, wherein said depending side wall of said second component comprises at least first and second outwardly flared sub-walls defining corresponding first and second interior lead-in surfaces for guiding said second component on said first component.

5. The petri dish of claim 4, wherein said first and second sub-walls are flared outward at first and second angles relative to each other.

6. A petri dish for containing a solidifiable culture media, comprising:
a first component having an imperforate bottom wall and an integral upstanding side wall around the periphery of the bottom wall opening opposite to said bottom wall; and
a second component having a top wall and an integral depending side wall so dimensioned to overlie and cover said first component, said depending side wall of said second component being flared outwardly relative to said top wall and from the juncture therewith to define at least one interior lead-in surface for guiding the depending wall of said second component over the upstanding wall of said first component and into mating engagement with the top wall at said juncture.

7. The petri dish of claim 6, wherein said depending side wall of said second component comprises at least first and second outwardly flared sub-walls defining corresponding first and second interior lead-in surfaces for guiding said second component on said first component.

8. The petri dish of claim 7, wherein said first and second sub-walls are flared outward at first and second angles relative to each other.

9. The petri dish of claim 6, wherein the bottom wall of said first component further comprises at least one groove formed therein at or adjacent to the periphery of the bottom wall, said groove for receiving and distributing a liquefied media during filling and for retaining the solidified media in place.

10. A petri dish for culturing microorganisms in a culture media contained in the dish comprising:
(A) a bottom cup member having an imperforate bottom and a peripheral side wall integral with the bottom wall to provide an open upper end for the cup member;
(B) a removable cover for the cup member comprising a planar wall and a circumferential side wall integral with the planar wall dimensioned to overlie said open end of the cup member;
(C) said bottom wall having an integral annular depending rib forming an annular distribution channel for fluidic culture media in the bottom cup member opening toward said open upper end; and
(D) said channel constructed and arranged to enable even spreading of said fluidic culture media and formation of a uniform meniscus thereof during manufacture of the petri dish.

11. The petri dish of claim 10 in which said channel is located at least adjacent the peripheral side wall of the bottom cup member.

12. The petri dish of claim 10 in which said planar wall has an integral upstanding rib dimensioned and located to be matingly engaged with the annular depending rib for stacking like petri dishes having said cover in place on a bottom cup member.

13. A petri dish as in claim 2 wherein, said second member has an upstanding peripheral rib on a top surface thereof, said rib being located in a parallel relationship with a top corner of said second member, and diametrically dimensioned such that an outside edge of said rib fits within a protruding exterior inwardly facing surface of said circumferential groove of said first member when said first member is placed directly on top of said second member.

14. A petri dish as in claim 13 wherein, said bottom wall is 25–30 percent thinner in thickness than said upstanding peripheral wall.

15. A petri dish as in claim 14 wherein, said second member has a top wall and a depending downwardly extending peripheral side wall, said top wall being 25–30 percent thinner in thickness than said side wall.

16. A petri dish as in claim 15 further comprising; a first thickened rim portion located on an edge portion of said upstanding peripheral wall.

17. A petri dish as in claim 16 further comprising; a second thickened rim portion located on an edge of said downwardly extending peripheral side wall.

18. A petri dish as in claim 2, further comprising: a plurality of standoffs located along an inner corner of said second member, such that a top edge portion of said upstanding peripheral wall only engages the standoffs located within said second member.

* * * * *